US007683080B2

(12) United States Patent
Liberman et al.

(10) Patent No.: US 7,683,080 B2
(45) Date of Patent: Mar. 23, 2010

(54) STABLE IANSOPRAZOLE CONTAINING MORE THAN 500 PPM, UP TO ABOUT 3,000 PPM WATER AND MORE THAN 200 PPM, UP TO ABOUT 5,000 PPM ALCOHOL

(75) Inventors: Anita Liberman, Tel-Aviv (IL); Claude Singer, Kfar Saba (IL); Irena Veinberg, Rehovot (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 10/717,325

(22) Filed: Nov. 18, 2003

(65) Prior Publication Data
US 2004/0215021 A1  Oct. 28, 2004

Related U.S. Application Data

(60) Provisional application No. 60/427,589, filed on Nov. 18, 2002, provisional application No. 60/445,219, filed on Feb. 5, 2003.

(51) Int. Cl.
*A61K 31/4439* (2006.01)
*C07D 401/12* (2006.01)

(52) U.S. Cl. ..................... 514/338; 546/273.7
(58) Field of Classification Search ............ 546/273.7; 514/338
See application file for complete search history.

(56) References Cited

U.S. PATENT DOCUMENTS

| 4,628,098 | A |  | 12/1986 | Nohara et al. |
| 4,689,333 | A |  | 8/1987 | Nohara et al. |
| 4,822,807 | A |  | 4/1989 | Topfmeier et al. |
| 5,578,732 | A |  | 11/1996 | Kato et al. |
| 6,002,011 | A |  | 12/1999 | Kato et al. |
| 6,180,652 | B1 |  | 1/2001 | Tsujii et al. |
| 6,268,502 | B1 |  | 7/2001 | Milac et al. |
| 6,313,303 | B1 |  | 11/2001 | Tagami et al. |
| 2003/0036554 | A1 | * | 2/2003 | Avrutov et al. ............ 514/338 |
| 2003/0138466 | A1 | * | 7/2003 | Bhagwat et al. ........... 424/401 |
| 2004/0192923 | A1 | * | 9/2004 | Singer et al. ............ 546/273.7 |
| 2004/0215021 | A1 | * | 10/2004 | Liberman et al. ........ 546/273.7 |

FOREIGN PATENT DOCUMENTS

| ES | 2 105 953 | 10/1997 |
| JP | 2002-2230 | 1/2004 |
| JP | 2002-160105 | 1/2004 |
| WO | WO 99/47514 | 9/1999 |
| WO | 01/21617 | * 3/2001 |
| WO | WO 01/68594 A1 | 9/2001 |
| WO | WO 2004/018454 | 3/2004 |

OTHER PUBLICATIONS

Vrecer et al., "Study of Influence of temperature, etc.," Farmacevtski Vestnik (Ljubljana) 1997, 48, pp. 242-243.*
Kotar et al., "Study of polymorphism, etc.," European Journal of Pharmaceutical Sciences, 1996, 4, S182.*
Halebian et al, "Pharmaceutical Applications, etc.," J of Pharmaceutical Sciences, 1969, 38, pp. 911-929.*
Chemical & Engineering News, Feb. 2003, pp. 32-35.*
Muzaffar et al., "Polymorphism and drug, etc.," J of Pharmacy (Lahore) 1979, 1(1), pp. 59-66.*
Jain et al., "Polymorphism in Pharmacy" Indian Drugs, 1986, 23(6), pp. 315-329.*
Taday et al., "Using Terahertz Pulse, etc.," J of Pharmaceutical Sciences, 92(4), Apr. 2003, pp. 831-838.*
Concise Encyclopedia, Walter de Gruter Berline, NY, 1994, pp. 872-873.*
Doelker, Ann. Pharm. Fr 2002, 60, pp. 161-176.*
Brittain et al., "Polymorphism in Pharmaceutical Solids", NY: Marcel Dekker, Inc., 1999, pp. 1-2, 185.*
Doelker, "Ann. Pharm. FR.,", 2002, 60:161-176, english translation pp. 1-39.*
Singhal et al., "Drug Polymorphism, etc.," Advanced Drug Delivery Reviews 56, p. 335-347 (2004).*
Tabata, et al., "Stabilization of a New Antiulcer Drug (Lansoprazole) in Solid Dosage Forms", Drug Development and Industrial Pharmacy, 18(3), 1437-47 (1992).
USP Forum, vol. 26(5) [Sep.-Oct. 2000].

* cited by examiner

*Primary Examiner*—Patricia L Morris
(74) *Attorney, Agent, or Firm*—Kenyon & Kenyon LLP

(57) ABSTRACT

The present invention provides a stable 2-(2-pyridylmethyl) sulfinyl-1H-benzimidazole (lansoprazole) comprising either greater than 500 ppm and not more than about 3,000 ppm water or greater than 200 ppm and not more than about 5,000 ppm alcohol, or both. The present invention provides a method of preparing a stable lansoprozole as well as a pharmaceutical composition containing same. The present invention further provides a method of purifying lansoprazole that is substantially free of sulfone and sulfide derivatives.

18 Claims, No Drawings

STABLE LANSOPRAZOLE CONTAINING MORE THAN 500 PPM, UP TO ABOUT 3,000 PPM WATER AND MORE THAN 200 PPM, UP TO ABOUT 5,000 PPM ALCOHOL

CROSS-REFERENCE TO RELATED APPLICATION

This application claims the benefit of U.S. Provisional Application Ser. Nos. 60/427,589 filed Nov. 18, 2002 and 60/445,219 filed Feb. 5, 2003, the disclosures of which are incorporated by reference in their entireties herein.

FIELD OF THE INVENTION

The present invention relates to a stable 2-(2-pyridylmethyl) sulfinyl-1H-benzimidazole (lansoprazole) compound, further comprising either greater than 500 ppm and not more than about 3,000 ppm water, or greater than 200 ppm and not more than about 5,000 ppm alcohol or both. The present invention relates to a method of preparing the same. The present invention also relates to a method of purifying a stable lansoprazole compound that is substantially free of sulfone and sulfide derivatives.

BACKGROUND OF THE INVENTION

Several substituted 2-(2-pyridylmethyl) sulfinyl-1H-benzimidazoles are known gastric proton pump inhibitors. These benzimidazole derivatives include omeprazole, lansoprazole, pantoprazole, and rabeprazole.

Lansoprazole is a reversible proton (acid) pump inhibitor. Lansoprazole per se is protected by U.S. Pat. No. 4,628,098 assigned to Takeda Chemical Industries, Ltd. Lansoprazole is known chemically as (2-[[[3-methyl-4-(2,2,2-trifluoro-ethoxy)-2-pyridinyl]methyl]sulfinyl]-1H-benzimidazole) and has the following chemical formula A:

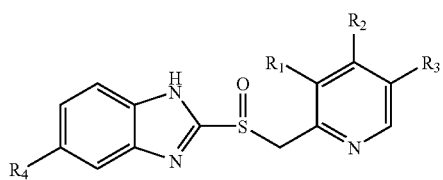

wherein $R_1$ is methyl, $R_2$ is trifluoro-ethoxy, and $R_3$ is hydrogen and $R_4$ is hydrogen. Other benzimidazole derivatives (e.g., omeprazole and pantoprazole) share lansoprazole's ability in inhibiting gastric acid secretion and they are commonly known as anti-ulcer agents.

The preparation of lansoprazole by conventional methods is always accompanied by the formation of small quantities of the corresponding sulfone derivative as an impurity. For example, U.S. Pat. No. 6,180,652 ("the '652 patent") describes the presence of sulfone derivative. Formation of sulfone derivative brings about the drawback of low yield of the desired sulfoxide. The '652 patent describes a method that permits separation of lansoprazole from its sulfone derivative and discloses an acetone complex of the lansoprazole salt.

U.S. Pat. No. 6,002,011 ("the '011 patent") discloses that lansoprazole and other 2-(2-pyridylmethyl) sulfinyl-benz-imidazole derivatives tend to lose stability and decompose when contaminated with traces of residual solvent, particularly in their crystal structure. According to the '011 patent, the residual solvent must be reduced to a minimum and it discloses a water reslurry method which provides a 'solvent-free' lansoprazole said to be more stable. Specifically, it limits the lansoprazole content to no more than 500 ppm water and 200 ppm $C_{1-6}$ alcohol.

The '011 patent also states that when an ethanol:water system is used to crystallize lansoprazole, it often contains solvent in excess of tolerable limits (i.e., more than 500 ppm water and more than 200 ppm alcohol) which causes the lansoprazole to be unstable. Efforts to eliminate this excessive solvent by intensive drying further destabilize the lansoprazole. As such, this prepared lansoprazole still contains intolerable levels of solvent and is unsuitable to be a pharmaceutical composition.

Reducing water and ethanol to levels below the reported tolerable limits (i.e., more than 500 ppm water and more than 200 ppm alcohol) is both time-consuming and costly.

In "Stabilization of a New Antiulcer Drug (Lansoprazole) in Solid Dosage Forms," by Tabata et al., *Drug Development and Industrial Pharmacy*, 18(13) 1437-47 (1992) (the 'Tabata article'), the mechanism of stabilization of lansoprazole in enteric granules is discussed. The Tabata article discloses that lansoprazole is unstable under conditions of high temperature and also high humidity, with a decrease in the amount of lansoprazole and discoloration of the material being noted on storage under such conditions. The variation in assay and color of solid lansoprazole over time on storage at various temperatures and humidities is presented in Table 2, at page 1439. The table shows that after 4 months at 40° C. and 75% room humidity lansoprazole turns pale brown, and even in the absence of humidity under the same conditions, lansoprazole turns pale yellowish brown. The Tabata article explains the unusually high instability of lansoprazole under even weak acidic conditions as being due to proton attack on the sulfoxide group. Lansoprazole seems to be especially sensitive to such attack compared to the other members of the 2-(2-pyridylmethyl) sulfinyl-benzimidazole family of drugs.

Lansoprazole is a relatively unstable compound, especially in acidic conditions, but also under strongly basic conditions. The Tabata article further discloses that degradation of lansoprazole is minimized under weakly basic conditions, and concludes that the degradation of lansoprazole in dosage forms is minimized by it being formulated to also contain stabilizing compounds suitable to produce such a weakly basic pH. The Tabata article, however, does not address the use of lansoprazole as an active pharmaceutical ingredient. As such, lansoprazole must be stored and transported, often for long time periods.

There is a continuing need to obtain a stable 2-(2-pyridylmethyl) sulfinyl-1H-benzimidazole (e.g., lansoprazole) that is free of contaminants (e.g., sulfone and sulfide derivatives) and a long-felt need for a pharmaceutical composition containing such a stable lansoprazole. In other words, the need exists for a stable form of lansoprazole, which does not suffer degradation and/or discoloration even if stored or transported under non-optimum conditions. The present invention provides such a stable lansoprazole compound and a method for its production.

SUMMARY OF THE INVENTION

The present invention provides a stable lansoprazole compound, further comprising greater than 500 ppm and not more than about 3,000 ppm water. Preferably, the stable lansoprazole compound comprises greater than about 600 ppm and not more than about 3,000 ppm water.

The present invention provides a stable lansoprazole compound, further comprising greater than 200 ppm and not more than about 5,000 ppm alcohol. Preferably, the stable lansoprazole compound comprises greater than about 300 ppm and not more than about 5,000 ppm alcohol.

The present invention provides a stable lansoprazole compound, further comprising greater than 500 ppm and not more than about 3,000 ppm water and greater than than 200 ppm and not more than about 5,000 ppm alcohol.

The present invention provides a method of preparing a stable lansoprazole compound, comprising the steps of:
 a) crystallizing a lansoprazole from an organic solvent or a mixture of organic solvent and water in the presence of an amine; and
 b) isolating a stable lansoprazole compound, wherein the stable lansoprazole compound further comprises greater than 500 ppm and not more than about 3,000 ppm water.

Preferably, the method provides a stable lansoprazole compound, further comprises greater than about 600 ppm and not more than about 3,000 ppm water.

The present invention provides a method of preparing a stable lansoprazole compound, comprising the steps of:
 a) crystallizing a lansoprazole from an organic solvent or a mixture of organic solvent and water in the presence of an amine; and
 b) isolating a stable lansoprazole compound, wherein the stable lansoprazole compound further comprises greater than 200 ppm and not more than about 5,000 ppm alcohol.

Preferably, the method provides a stable lansoprazole compound, further comprises greater than about 300 ppm and not more than about 5,000 ppm alcohol.

The present invention provides a method of preparing a stable lansoprazole compound, comprising the steps of:
 a) crystallizing a lansoprazole from an organic solvent or a mixture of organic solvent and water in the presence of an amine; and
 b) isolating a stable lansoprazole compound, wherein the stable lansoprazole compound further comprises greater than 500 ppm and not more than about 3,000 ppm water, and greater than 200 ppm and not more than about 5,000 ppm alcohol.

A method of purifying a lansoprazole compound, comprising the steps of:
 a) crystallizing a lansoprazole from an organic solvent or a mixture of organic solvent and water in the presence of an amine; and
 b) isolating a crystallized lansoprazole compound, wherein the crystallized lansoprazole compound further comprises less than about 0.1% (wt/wt) sulfone derivative and less than about 0.1% sulfide derivative (wt/wt) sulfide derivative.

Preferably, the method, after step a), further comprises the step of washing the crystallized lansoprazole compound in an acetone-water mixture. More preferably, the pH of the acetone-water mixture is adjusted to a pH of about 8 to about 10. More preferably, the pH of the acetone-water mixture is adjusted to a pH of 9.

Preferably, the isolating step comprises the step of drying the crystallized lansoprazole compound in the presence of a weakly basic gas. More preferably, the weakly basic gas is ammonia or methylamine.

The present invention also provides a pharmaceutical composition comprising a stable lansoprazole.

More preferably, the present invention provides a stable lansoprazole compound that is substantially free of sulfone and sulfide (i.e., containing less than about 0.1% (wt/wt) sulfone derivative and less than about 0.1% (wt/wt) sulfide derivative).

DETAILED DESCRIPTION OF THE INVENTION

Definition:

"LNPS" refers to the sulfide-containing starting compound for lansoprazole preparation. The chemical name for LNPS is 2-[[3-methyl-4-(2,2,2-trifluoroethoxy)-2-pyridyl]thio]-1H benzimidazole. "LNP" refers to lansoprazole which has the chemical name of 2-[[3-methyl-4-(2,2,2-trifluoroethoxy)-2-pyridyl]methyl]sulfinyl-1H benzimidazole. The present invention provides a lansoprazole substantially free of sulfone and sulfide (i.e., containing less than about 0.1% (wt/wt) sulfone derivative and less than about 0.1% (wt/wt) sulfide derivative). A "stable" lansoprazole refers to a lansoprazole that is stable (e.g., limited decomposition) under specified storage conditions (i.e., 2-8° C. or 25° C. at a relative humidity of up to 60% for a time period of up to about 6 months). In other words, a "stable" lansoprazole does not undergo discoloration and remains substantially free of sulfone and sulfide (i.e., containing less than about 0.1% (wt/wt) sulfone derivative and less than about 0.1% (wt/wt) sulfide derivative) under these specified storage conditions.

Unless otherwise stated, % refers to % (wt/wt); "<" refers to less than; ">" refers to greater than; "ppm" refers to parts per million.

The alcohol mentioned within this application includes $C_{1-6}$ alcohols (e.g., methanol, ethanol, isopropyl alcohol, and the like.). Preferably, the alcohol is ethanol.

In accordance with the present invention, 2-[[3-methyl-4-(2,2,2-trifluoro ethoxy)-2-pyridyl]thio]-1H benzimidazole is used as a starting material for preparation of 2-[[3-methyl-4-(2,2,2-trifluoroethoxy)-2-pyridyl]methyl]sulfinyl-1H benzimidazole and is dissolved in an organic solvent or a mixture of organic solvent with water.

The exemplary organic solvents include $C_{1-6}$ alcohol such as ethanol, methanol, n-propanol, and i-propanol, as well as dimethyl-carbonate, diethyl-carbonate, acetone, 2-butanone, dimethyl-formamide, tetrahydrofuran and mixtures thereof. Preferably, the organic solvent is ethanol.

In the present invention, crystallization of lansoprazole in an organic solvent is performed in the presence of an amine to result in lansoprazole substantially free of sulfone and sulfide. An amine is an organic compound containing nitrogen, and includes any member of a group of chemical compounds formed from ammonia by replacement of one or more of the hydrogen atoms by organic (hydrocarbon) radicals. The amines may be primary, secondary or tertiary, dependent on whether one, or two or three hydrogen atoms are replaced. Exemplary amine compounds include ammonia, ammonium hydroxide, diethylamine, triethylamine, methylamine, diethanolamine, triethanolamine and mixtures thereof. Preferably, the amine is ammonium hydroxide.

Preferably, ammonium hydroxide is present at a mol/mol ratio to lansoprazole of about 7 to about 1. Most preferably, the ammonium hydroxide is present at a mol/mol ratio to lansoprazole of greater than about 1. Crystallization of lansoprazole under such conditions permits a good separation of lansoprazole from impurities, especially sulfone and/or sulfide derivatives.

In the present invention, precipitation of lansoprazole can be achieved by acidifying the solution of lansoprazole in organic solvent or a mixture of organic solvent and water. At lower temperatures, a partial precipitation of lansoprazole may take place even in the absence of an acid. The added acid can neutralize the ammonium hydroxide during the crystallization of lansoprazole.

Exemplary acids used to crystallize lansoprazole include acetic acid, formic acid, hydrochloric acid (HCl) and mixtures thereof. Preferably, the acid is acetic acid.

Although the lansoprazole obtained by the above-mentioned crystallization process can be advantageous, it cannot be dried to <0.1% water as required by the USP forum. As mentioned previously, water can have a negative impact on the long-term stability of lansoprazole (the '011 patent). The '011 patent explicitly states that lansoprazole containing water at a level more than 500 ppm is unstable; and lansoprazole containing ethanol at a level more than about 200 ppm is unstable. The '011 patent teaches the water content of lansoprazole can be reduced to by recrystallization from organic solvent.

Preferably, the lansoprazole is completely dissolved in the solvent before recrystallization. The dissolution of lansoprazole can be accelerated by the presence of small amounts of water. The presence of water can be insured by using wet lansoprazole from the previously mentioned purification step or by adding <20% (vol/vol) water to the solvent.

The dissolution of lansoprazole can be performed at the solvent reflux temperature. Preferred dissolution temperatures should be lower than the reflux temperature, given the instability of lansoprazole at higher temperatures. Preferably, the dissolution temperature does not exceed 50° C.

According to the present invention, a lansoprazole compound that comprises either greater than 500 ppm and not more than about 3,000 ppm water, or greater than 200 ppm and not more than about 5,000 ppm alcohol or both, is stable during storage. Therefore, it is not necessary to continue the drying at elevated temperatures, which may adversely affect the purity of lansoprazole. Also, it is not necessary to reprocess lansoprazole by the additional steps such as disclosed in the '011 patent, which may adversely affect the overall yield of the preparation process.

The crystallization yield of lansoprazole can be improved by cooling or by removing solvent or water from the crystallization system. One skilled in the art would appreciate the techniques that are used to remove water from a mixture of organic solvent and water, e.g., azeotropic distillation.

Following crystallization, the precipitated lansoprazole may be washed prior to crystallization. Washing is carried out by use of an acetone-water mixture to which is added a sufficient amount of a weakly basic solution to bring the pH of the resulting washing solution to from about 8 to about 10. Most preferably, the pH of the washing solution is about 9. Other solvents that can be used include dimethyl-carbonate, diethyl-carbonate and mixtures thereof.

Following washing, the precipitated lansoprazole may be dried by conventional means, taking into account that at elevated temperatures lansoprazole is unstable. In the present invention, the drying process is performed in the presence of a weakly basic gas. Preferably, a weakly basic gas may include ammonia, methylamine and mixtures thereof. More preferably, the weakly basic gas is ammonia.

Pharmaceutical Formulations and Dosages

The present invention also provides a stable pharmaceutical formulation comprising a stable lansoprazole. When a lansoprazole compound further comprises either greater than 500 ppm and not more than about 3,000 ppm water, or greater than 200 ppm and not more than about 5,000 ppm ethanol, or both, this amount of water and ethanol actually stabilize the lansoprazole.

In accordance with the present invention, the stable lansoprazole compound may be formulated into a variety of pharmaceutical compositions and dosage forms for therapeutic uses, especially for the treatment of stomach ulcers.

In addition to the active ingredient(s), lansoprazole pharmaceutical compositions of the present invention may contain one or more pharmaceutically acceptable excipients. Excipients are added to the composition for a variety of purposes.

Diluents increase the bulk of a solid pharmaceutical composition and may make a pharmaceutical dosage form containing the composition easier for the patient and caregiver to handle. Diluents for solid compositions include, for example, microcrystalline cellulose (e.g. AVICEL®, microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form like a tablet may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. KLUCEL®), hydroxypropyl methyl cellulose (e.g. METHOCEL®), liquid glucose, magnesium aluminum silicate, maltodextrin, methylcellulose, polymethacrylates, povidone (e.g. KOLLIDON®, PLASDONE®), pregelatinized starch, sodium alginate and starch. The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. AC-DI-SOL®, PRIMELLOSE®), colloidal silicon dioxide, crosscarmellose sodium, crospovidone (e.g. KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g. EXPLOTAB®) and starch.

Glidants can be added to improve the flow properties of non-compacted solid compositions and improve the accuracy of dosing. Excipients that may function as glidants include colloidal silicon dioxide, magnesium trisilicate, powdered cellulose, starch, talc and tribasic calcium phosphate.

When a dosage form such as a tablet is made by compaction of a powdered composition, the composition is subjected to pressure from a punch and die. Some excipients and active ingredients have a tendency to adhere to the surfaces of the punch and die, which can cause the product to have pitting and other surface irregularities. A lubricant can be added to the composition to reduce adhesion and ease release of the product from the die. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate. Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid ethyl maltol, and tartaric acid.

Compositions may also be colored using any pharmaceutically acceptable colorant to improve their appearance and/or facilitate patient identification of the product and unit dosage level.

Selection of excipients and the amounts to use may be readily determined by formulation scientists based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and lozenges as well as liquid syrups, suspensions and elixirs. An especially preferred dosage form of the present invention is a tablet.

Tablets, capsules, lozenges and other unit dosage forms preferably contain lansoprazole in a dosage level of from about 50 to about 300 mg, more preferably about 200 mg.

The following non-limiting examples illustrate the invention:

EXAMPLE 1

Preparation of Lansoprazole Crude

Into a flask, 1 L ethanol (95%) was charged and cooled under stirring to 5° C. Under mixing, 200 grams 2-[[3-methyl-4-(2,2,2-trifluoroethoxy)-2-pyridyl]thio]-1H benzimidazole (LNPS) and 3 grams vanadium acetyl acetonate were added. 110 grams tert-butyl-hydroperoxide solution was dropped slowly into the suspension. The suspension was maintained under mixing for 6 hours.

40 grams $Na_2SO_3$ dissolved in 400 ml water were added. 1 L of water (pH=8-8.5, realized by the addition of $NH_4OH$) was added. The suspension was further mixed for 17 hours at 25° C. The suspension was then cooled to 5° C. The solid phase was separated by vacuum filtration and then was dried. 178 grams of LNP crude was obtained (yield: 85%).

Sulfone: 0.15% (wt/wt)
LNPS: 0.3% (wt/wt)

EXAMPLE 2

Purification of Lansoprazole

In a 0.25 L flask, 67.5 ml ethanol (95%), 15 ml ammonia (24%) and 45 ml water were charged. The suspension was cooled under stirring to 5° C. Under mixing, 10 grams lansoprazole crude were added and heated to 52° C. until dissolved. 1 gram of active carbon was added to the slightly turbid solution and maintained for a short time at 49° C.

The active carbon was then separated-on a filter and the cake was washed with a mixture of 14 ml ethanol and 12 ml water. The solution was cooled and lansoprazole was precipitated by the addition of 3.75 ml acetic acid. The suspension was then cooled to 10° C. and filtered.

The product (wet lansoprazole) was washed with water and ethanol. Subsequently, the washed wet lansoprazole product was dried (vacuum/50° C./17 hours). 8.7 grams of lansoprazole (pure) was obtained (yield: 89%).

Sulfone: 0.05% (wt/wt)
LNPS: below the detection limit

Water content as determined by Karl Fisher (KF) method was 2,200 ppm. The product of Example 2 cannot be dried to <0.1% (wt/wt) water but can be dried to about 0.18% (wt/wt) water.

Alcohol content as determined by gas chromatography (GC) was <50 ppm.

The obtained lansoprazole is stable. The stability of the lansoprazole was determined at different temperatures and relative humidities as shown in Table 1.

TABLE 1

Stability of Lansoprazole under Different Conditions

| Time | Temperature ° C. | Humidity % | LNP-SO2[1] % | LNPS[2] % | Total Impurities % |
|---|---|---|---|---|---|
| 0 | — | — | 0.04 | <detection limit | 0.04 |
| 2 weeks | 25 | 60 | 0.04 | <detection limit | 0.04 |
| 1 month | 2-8 | — | 0.04 | 0.01 | 0.05 |
|  | 25 | 60 | 0.04 | 0.01 | 0.09 |
| 2 month | 2-8 | — | 0.04 | 0.01 | 0.05 |
|  | 25 | 60 | 0.04 | 0.01 | 0.08 |
| 3 month | 2-8 | — | 0.04 | <detection limit | 0.04 |
|  | 25 | 60 | 0.04 | <detection limit | 0.1 |
| 6 month | 2-8 | — | 0.04 | <detection limit | 0.04 |
|  | 25 | 60 | 0.04 | <detection limit | 0.12 |
| 9 month | 2-8 | — | 0.05 | <detection limit | 0.05 |
|  | 25 | 60 | 0.05 | 0.04 | 0.18 |
| 12 month | 2-8 | — | — | <detection limit | 0.03 |
|  | 25 | 60 | 0.04 | 0.07 | 0.32 |

[1] 2-[[3-methyl-4-(2,2,2-trifluoroethoxy)-2-pyridyl]sulfonyl]-1H benzimidazole
[2] 2-[[3-methyl-4-(2,2,2-trifluoroethoxy)-2-pyridyl]thio]-1H benzimidazole Chromatographic purity method of lansoprazole is detailed in the monograph in USP Forum Vol.26(5) [September-October 2000].

HPLC Condition:

| | |
|---|---|
| Column: | C18 |
| Mobile phase: | Gradient of triethylamine in water with acetonitrile |
| Flow: | 0.8 ml/min |
| Detection: | 285 nm |

Karl Fisher (KF) method for water determination is the USP method <921>Ia with the solvent:pyridine and ethylene glycol 9:1 as detailed in USP Forum Vol.26(5) [September-October 2000].

EXAMPLE 3

Purification of Lansoprazole (Different Drying Conditions)

In a 0.25L flask, 67.5 ml ethanol (95%), 15 ml ammonia (24%) and 45 ml water were charged. The suspension was cooled under stirring to 5° C. Under mixing, 10 grams lansoprazole crude were added and heated to 52° C. until dissolved. 1 gram of active carbon was added to the slightly turbid solution and maintained for a short time at 49° C.

The active carbon was then separated on a filter and the cake was washed with a mixture of 14 ml ethanol and 12 ml water. The solution was cooled and lansoprazole was precipitated by the addition of 3.75 ml acetic acid. The suspension was then cooled to 10° C. and filtered.

The wet lansoprazole product was washed with water and ethanol. Subsequently, the washed wet lansoprazole product was subjected to the following drying conditions:

| Experiment no | Drying conditions | Water content (by KF) ppm |
|---|---|---|
| 3(a) | Vacuum/40° C./17 hours | 2,700 |
| 3(b) | Vacuum/44° C./24 hours | 2,300 |
| 3(c) | Similar to Example 5 (see below) (under vacuum in the presence of a weak $NH_3$ flow at 45° C.) | 1,800 |
| 3(d) | Similar to Example 5 (see below) but i-propanol instead of ethanol in crystallization | 2,500 |
| 3(e) | Suspension in toluene and azeotropic removal of water | 2,900 |
| 3(f) | Dry distillation of solvent | 1,900 |

EXAMPLE 4

In this experiment, the same procedure as in Example 2 is repeated up to the washing step of the wet lansoprazole (i.e., prior to the drying step). The water and alcohol contents of the obtained wet lansoprazole product are determined (prior to the drying step). The water content should be about 2,200 ppm, and the content of ethanol should be about 300 ppm to about 500 ppm. The wet lansoprazole product should behave similarly to the dry lansoprazole as detailed in Example 2 with respect to stability.

EXAMPLE 5

Crystallization of Lansoprazole

Into a 0.25L flask was charged 29.8 grams wet lansoprazole, prepared according to Example 2, and 30 ml acetone. The suspension was heated to 52° C. and 150 ml acetone added dropped until a clear solution was obtained. The solution was cooled to 10° C. and concentrated until the weight of the reaction mass was 48.5 grams. The solid was separated by filtration and washed with 20 ml cold acetone water mixture, the pH of which was corrected to 9±1 by addition of ammonium hydroxide solution (25%). Lansoprazole was dried under vacuum in the presence of a weak $NH_3$ flow at 45° C.

18.58 grams product was obtained (yield 91%)

Water content: 0.05 % (wt/wt), by Karl Fischer method.

The water content of additional dried lansoprazole samples (obtained by repeating the procedure in this example) was further determined to be within the range of about 200 ppm to about 800 ppm (i.e., less than about 1,000 ppm).

The stability of the lansoprazole was further determined at different temperatures and relative humidities as shown in Table 2:

TABLE 2

Stability of Stabilized vs. Non-Stabilized 'Solvent-Free' Lansoprazole

| Time | Temperature ° C. | Humidity % | LNP-SO2[1] % | LNPS[2] % | Total Impurities % | Color |
|---|---|---|---|---|---|---|
| Lansoprazole Not Stabilized With Ammonia | | | | | | |
| 3 months | 40 | 75 | 0.04 | 0.06 | 0.31 | Brownish |
| Lansoprazole Stabilized With Ammonia | | | | | | |
| 3 months | 40 | 75 | 0.02 | 0.03 | 0.08 | White |

[1] 2-[[3-methyl-4-(2,2,2-trifluoroethoxy)-2-pyridyl]sulfonyl]-1H benzimidazole
[2] 2-[[3-methyl-4-(2,2,2-trifluoroethoxy)-2-pyridyl]thio]-1H benzimidazole Chromatographic purity method of lansoprazole is detailed in the monograph in USP Forum Vol.26(5) [September-October 2000].

HPLC Condition:

| Column: | C18 |
|---|---|
| Mobile phase: | Gradient of triethylamine in water with acetonitrile |
| Flow: | 0.8 ml/min |
| Detection: | 285 nm |

Karl Fisher (KF) method for water determination is the USP method <921>Ia with the solvent:pyridine and ethylene glycol 9:1 as detailed in USP Forum Vol.26(5) [September-October 2000].

Other solvents that can be used in lieu of acetone include dimethyl-carbonate and diethyl-carbonate.

A number of embodiments of the invention have been described. The present invention is not to be limited in scope by the specific embodiments described herein. It will be understood that various modifications may be made without departing from the spirit and scope of the invention. Various publications and patents are cited herein, the disclosures of which are incorporated by reference in their entireties.

What is claimed is:

1. Chemically stable lansoprazole comprising greater than 500 ppm and not more than about 3,000 ppm water, wherein lansoprazole is stable at a temperature of from 2° C. to 8° C. or at 25° C. at a relative humidity of up to 60% for a period of up to about 6 months.

2. The chemically stable lansoprazole of claim 1, wherein the chemically stable lansoprazole comprises greater than about 600 ppm and not more than about 3,000 ppm water.

3. Chemically stable lansoprazole comprising greater than 200 ppm and not more than about 5,000 ppm alcohol, wherein lansoprazole is stable at a temperature of from 2° C. to 8° C. or at 25° C. at a relative humidity of up to 60% for a period of up to about 6 months.

4. The chemically stable lansoprazole compound of claim 3, wherein the chemically stable lansoprazole comprises greater than about 300 ppm and not more than about 5,000 ppm alcohol.

5. Chemically stable lansoprazole comprising greater than 500 ppm and not more than about 3,000 ppm water, and greater than 200 ppm and not more than about 5,000 ppm alcohol, wherein lansoprazole is stable at a temperature of from 2° C. to 8° C. or at 25° C. at a relative humidity of up to 60% for a period of up to about 6 months.

6. The chemically stable lansoprazole as in one of claims 1 to 5, further comprising less than about 0.1% (wt/wt) 2-[[3- methyl-4-(2,2,2-trifluorethoxy)-2-pyridinyl]sulfonyl]-1H benzimidazole and less than about 0.1% (wt/wt) 2-[[3-methyl-4-(2,2,2-trifluorethoxy)-2-pyridinyl]thio]-1H benzimidazole.

7. A pharmaceutical composition, comprising chemically stable lansoprazole and a pharmaceutically acceptable excipient, wherein the chemically stable lansoprazole comprises greater than 500 ppm and not more than about 3,000 ppm water and is stable at a temperature of from 2° C. to 8° C. or at 25° C. at a relative humidity of up to 60% for a period of up to about 6 months.

8. The pharmaceutical composition of claim 7, wherein the chemically stable lansoprazole comprises greater than about 600 ppm and not more than about 3,000 water.

9. A pharmaceutical composition comprising chemically stable lansoprazole and a pharmaceutically acceptable excipient, wherein the chemically stable lansoprazole comprises greater than 200 ppm and not more than about 5,000 ppm alcohol and is stable at a temperature of from 2° C. to 8° C. or at 25° C. at a relative humidity of up to 60% for a period of up to about 6 months.

10. The pharmaceutical composition of claim 9, wherein the chemically stable lansoprazole comprises greater than about 300 ppm and not more than about 5,000 ppm alcohol.

11. A pharmaceutical composition comprising chemically stable lansoprazole and a pharmaceutically acceptable excipient, wherein the chemically stable lansoprazole comprises greater than 500 ppm and not more than about 3,000 ppm water and greater than 200 ppm and not more than about 5,000 ppm alcohol and is stable at a temperature of from 2° C. to 8° C. or at 25° C. at a relative humidity of up to 60% for a period of up to about 6 months.

12. The pharmaceutical composition as in any one of claims 7 to 11, wherein the chemically stable lansoprazole comprises less than about 0.1% (wt/wt) 2-[[3-methyl-4-(2,2,2-trifluorethoxy)-2-pyridinyl]sulfonyl]-1H benzimidazole and less than about 0.1% (wt/wt) 2-[[3-methyl-4-(2,2,2-trifluorethoxy)-2-pyridinyl]thio]- 1H benzimidazole.

13. The pharmaceutical composition as in any one of claims 7 to 11, wherein the pharmaceutical composition is in a dosage form selected from the group consisting of tablets, powders, capsules, suppositories, sachets, troches, lozenges, liquid syrups, suspensions and elixirs.

14. The pharmaceutical composition as in any one of claims 7 to 11, wherein the pharmaceutical composition is a tablet.

15. The pharmaceutical composition as in any one of claims 7 to 11, wherein the pharmaceutical composition comprises chemically stable lansoprazole in a dosage level of from about 50 to about 300 mg.

16. The pharmaceutical composition as in any one of claims 7 to 11, wherein the pharmaceutical composition comprises chemically stable lansoprazole in a dosage level of about 200 mg.

17. The chemically stable lansoprazole as in claim 6, comprising less than about 0.05% (wt/wt) 2-[[3-methyl-4-(2,2,2-trifluorethoxy)-2-pyridinyl]sulfonyl]-1H benzimidazole and less than about 0.05% (wt/wt) 2-[[3-methyl-4-(2,2,2-trifluorethoxy)-2-pyridinyl]thio]-1H benzimidazole.

18. The pharmaceutical composition as in claim 12, wherein the chemically stable lansoprazole comprises less than about 0.05% (wt/wt) 2-[[3-methyl-4-(2,2,2-trifluorethoxy)-2-pyridinyl]sulfonyl]-1H benzimidazole and less than about 0.05% (wt/wt) 2-[[3-methyl-4-(2,2,2-trifluorethoxy)-2-pyridinyl]thio]-1H benzimidazole.

* * * * *